Dec. 1, 1964 J. GAUJARD Plant Pat. 2,455
ROSE PLANT
Filed May 6, 1963
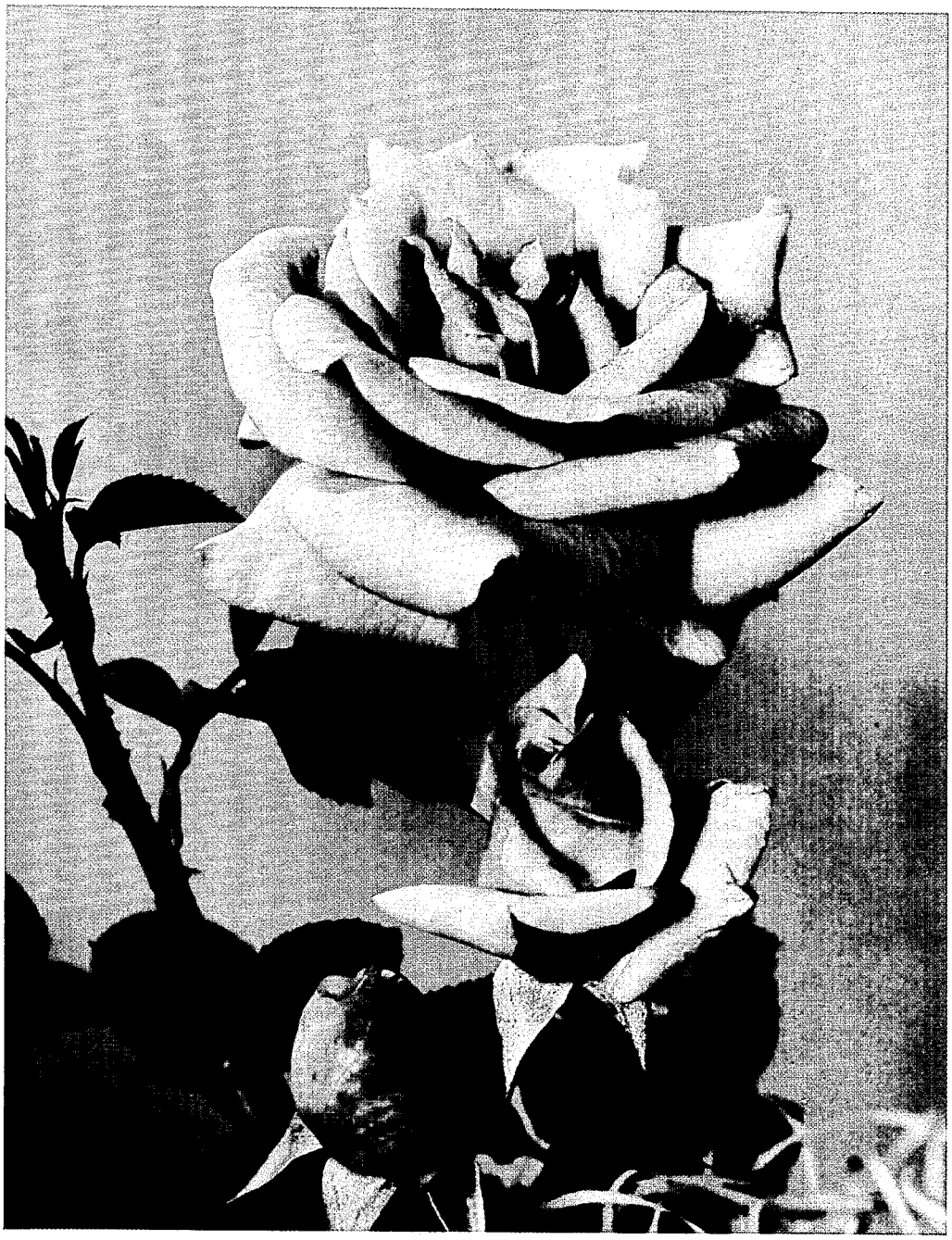
Inventor
Jean Gaujard
By: Robb & Robb
Attorneys.

United States Patent Office

Plant Pat. 2,455

Patented Dec. 1, 1964

2,455

ROSE PLANT

Jean Gaujard, Feyzin, France, assignor to Ilgenfritz Nurseries, Inc., Monroe, Mich., a corporation of Michigan Filed May 6, 1963, Ser. No. 278,501
1 Claim. (Cl. Plt.—11)

The present invention relates to a new and distinct variety of rose plant of the hybrid tea class, which was originated by me by crossing the variety "Peace" (U.S. Plant Patent No. 591), known in France as "Mme. A. Meilland," with the variety "Viola" (unpatented).

As the result of this breeding, I have produced a new and improved rose variety which is distinguished from its parents, as well as from all other varieties of which I am aware, as evidenced by the following unique combination of characteristics which are outstanding therein:

(1) A very vigorous habit of growth;

(2) Large flowers;

(3) A distinctive and attractive Bishop's Violet general color tonality of the flowers which are darker colored than the flowers of any other variety in commerce in this color range; and (4) An exceptionally strong and penetrating flower fragrance.

Asexual reproduction of the new variety by budding, as performed by me at Feyzin, France, shows that the aforementioned characteristics and distinctions come true to form and are established and transmitted through succeeding propagations.

The accompanying drawing shows typical specimens of the vegetative growth and flowers of my new variety as depicted in color as nearly true as it is reasonably possible to make the same in a color illustration of this character.

The following is a detailed description of my new variety, with color terminology in accordance with the color chart entitled "Repertoire de Couleurs," prepared by Rene Oberthur, except where general color terms of ordinary dictionary significance are obvious:

Type: Hardy; bush; greenhouse; outdoor; for cut flowers and for garden decoration.

Class: Hybrid tea.

Breeding: Seedling.

*Seed parent.*—"Peace."

*Pollen parent.*—"Viola."

Propagation: Holds its distinguishing characteristics through succeeding propagations by budding.

*Flower*

Locality where grown and observed; Outdoors at Feyzin, France and in greenhouse at Antibes, France.

Flowers borne: Singly and in regular clusters; on strong, long stems.

Quantity of bloom: Free, both outdoors and in greenhouse; flowers are very large in greenhouse.

Continuity: Continuous.

Fragrance: Strong and penetrating.

Bud:

*Peduncle.*—Long; erect; stiff; smooth, few green prickles. Color—green.

*Before calyx breaks.*—Size—large. Form—long; pointed; without foliaceous appendages on the surface of the bud; with stout foliaceous parts extending beyond the tip of the bud equal to ¼ or more of its length. Color—Bishop's Violet, No. 3, page 189.

*As calyx breaks.*—Color—Bishop's Violet, No. 2, page 189.

*As first petal opens.*—Size—large. Form—long; pointed. Color: outside—Bishop's Violet, No. 3, page 189; inside—Bishop's Violet, No. 2, page 189.

*Opening.*—Opens up well; is retarded by wet weather.

Bloom:

*Size (when fully open).*—Large; from 5 inches to 6 inches.

*Petalage.*—Double; from 35 to 45 petals; arranged regularly.

*Form.*—High-centered at first; petals being at first tightly rolled outward, and remaining rolled outward at maturity.

Petals:

*Texture.*—Thick.

*Appearance.*—Inside—from shiny to satiny. Outside—from shiny to satiny.

*Shape.*—Outside—oval. Intermediate—oval. Inside—oval.

This description of a newly opened flower was made from a rose grown outdoors in the month of September at Feyzin, France:

*Color.*—Outer petal: outside surface—Bishop's Violet, No. 3, page 189; inside surface—Bishop's Violet, No. 2, page 189. Intermediate petal: outside surface—Bishop's Violet, No. 3, page 189; inside surface—Bishop's Violet, No. 2, page 189. Inner petal: outside surface—Bishop's Violet, No. 2, page 189; inside surface—Bishop's Violet, No. 1, page 189.

This description was made of a rose that was open for three days in a greenhouse during the month of September at St. Remy de Provence, France:

*Color.*—Outer petal: outside surface—Bishop's Violet, No. 2, page 189; inside surface—Bishop's Violet, No. 1, page 189. Inner petal: outside surface—Bishop's Violet, No. 2, page 189; inside surface—Bishop's Violet, No. 1, page 189.

*General color effect.*—Newly opened flower—Bishop's Violet, No. 1, page 189. 3-days open—Bishop's Violet, No. 1, page 189.

*Behavior.*—Very good in hot weather and in dry climate; blooms are sometimes shaded with pink in the finishing stage.

*Flower longevity.*—On bush in garden—10 days in September. Cut roses grown outdoors and kept at living-room temperatures—10 days in September. Cut roses grown in greenhouse and kept at living-room temperatures—7 days in September.

*Reproductive Organs*

Stamens: Medium number; arranged regularly about pistils; tucked in calyx. Color—clear yellow.

Filaments: Long; many with anthers. Color—white.

Anthers: Large; all open at once. Color—yellow.

Pollen: Abundant quantity. Color—yellow.

Pistils: Many.

Styles: Even; medium length; separated.

Stigma: Color—yellow.

Ovaries: All enclosed in calyx.

Hips: Short; globular; moderately thick. Color—green-scarlet.

Sepals: Falling soon; long; recurved. Color—natural green-grey.

Seeds: Many; large.

*Plant*

Foliage:

*Leaves.*—Compound of 5 leaflets; abundant quantity; large size; heavy.

*Leaflets.*—Shape—oval. Base—round. Margin—simply serrate.

*Color.*—Mature: upper surface—normal green;

under surface—green. Young: upper surface—moderately green; under surface—normal green.

*Rachis (the supporting stem of the compound leaf).*—Medium size. Upper side—hairy. Under side—hairy.

*Stipules.*—Long; with long points turning out at an angle of less than 45°.

*Disease resistance.*—Good resistance to mildew and blackspot, as determined by comparison with other varieties grown in France under the same cultural conditions.

Growth:

*Habit.*—Bushy; much-branched.

*Growth.*—Free; vigorous.

*Canes.*—Heavy.

*Main steams.*—Color—green. Thorns—few; long; with short, round base. Prickles—few. Hairs—few; color—grey.

*Branches.*—Color—green. Thorns—few; with short, round base. Prickles—few; color—grey. Hairs—several; color—green.

*New shoots.*—Color—dull bronze. Thorns—few; long; straight; with narrow, round base. Prickles—few; color—grey. Hairs—few; color—green.

I claim:

A new and distinct variety of rose plant of the hybrid tea class, substantially as herein shown and described, characterized particularly as to novelty by the unique combination of a very vigorous habit of growth, large flowers, a distinctive and attractive Bishop's Violet general color tonality of the flowers, and an exceptionally strong and penetrating flower fragrance.

No references cited.

ABRAHAM G. STONE, *Primary Examiner.*